United States Patent
Santi et al.

(10) Patent No.: US 6,281,397 B1
(45) Date of Patent: *Aug. 28, 2001

(54) CATALYTIC COMPOSITION FOR THE HYDROGENATION OF OLEFINICALLY UNSATURATED ORGANIC COMPOUNDS

(75) Inventors: Roberto Santi, Novara; Francesco Masi, S. Angelo Lodigiano-Lodi; Gianfranco Longhini, Vercelli, all of (IT)

(73) Assignee: Enichem S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,378

(22) Filed: Jan. 22, 1999

(30) Foreign Application Priority Data

Jan. 27, 1998 (IT) ............................................. MI98A0137

(51) Int. Cl.[7] ................................................... C07C 13/00
(52) U.S. Cl. ......................... 585/250; 585/266; 585/269; 585/271; 585/273; 585/275
(58) Field of Search ................................... 585/250, 266, 585/269, 271, 273, 275

(56) References Cited

U.S. PATENT DOCUMENTS 4,380,508    4/1983    Shipley et al. .
4,472,523    9/1984    Welch et al. .

FOREIGN PATENT DOCUMENTS 137 329      8/1979    (DE) .
0 298 408    1/1989    (EP) .

OTHER PUBLICATIONS

Martin F. Sloan, et al., Journal Of The American Chemical Society, vol. 85, pp. 4014–4018, "Soluble Catalysts for the Hydrogenation of Olefins", Dec. 20, 1963.

*Primary Examiner*—Paul J. Killos
(74) *Attorney, Agent, or Firm*—Oblon, Spivak, McClelland, Maier & Neustadt, P.C.

(57) ABSTRACT

A catalytic composition effective in the selective hydrogenation of olefinic double bonds, comprising the reaction product between:

(A) at least one complex of a transition metal having the following general formula (I):

$$M(R^1)(R^2)(R^3)(R^4) \qquad (I)$$

wherein: M is selected from titanium and zirconium, preferably titanium;
each of the radicals $R^1$, $R^2$, $R^3$ or $R^4$, independently, represents an organic or inorganic group of an anionic nature σ-bound to M, on the condition that at least one, and preferablyat at least two, of these radicals is an organic group; and (B) at least one organometallic compound of magnesium having the following formula (II):

$$Mg(R^5)_n(R^6)_{(2-n)} \qquad (II)$$

wherein: $R^5$ or $R^6$ each independently represent an aliphatic or aromatic hydrocarbon group having from 1 to 20 carbon atoms, and
"n" is a decimal number between 0 and 2.0.

Said catalytic composition advantageously and selectively promotes the direct hydrogenation of double bonds of an olefinic type, with high rates and with a reduced formation of isomers.

14 Claims, No Drawings

CATALYTIC COMPOSITION FOR THE HYDROGENATION OF OLEFINICALLY UNSATURATED ORGANIC COMPOUNDS

The present invention relates to a catalyst for the hydrogenation of olefinically unsaturated compounds, comprising at least one compound of titanium.

More specifically, the present invention relates to a process for the selective hydrogenation of unsaturated compounds containing at least one olefinic double bond, and a catalyst based on non-cyclopentadienyl derivatives of titanium combined with a suitable co-catalyst.

The hydrogenation of unsaturated substrates is a technology widely-used for obtaining products which can be used in various fields, from the food industry to the field of plastic materials and the like. Several methods are known for the hydrogenation of olefinic double bonds (chemically a reduction by means of hydrogen), most of which use gaseous hydrogen in the presence of a suitable catalyst. The latter normally comprises a transition metal, usually a metal of group 10 of the periodic table, i.e. Ni, Pd or Pt. If these are present as impurities in the hydrogenated substrate, they can cause aging phenomena or toxicological problems in the case of food.

Catalysts normally used comprise:
(1) supported heterogeneous catalysts consisting of inert materials (for example silica, alumina, carbon) onto which a metal such as nickel, platinum, palladium, etc. is deposited, and
(2) non-supported catalysts obtained by reacting an organometallic compound of nickel, cobalt, titanium, etc., with a reducing compound such as an organoaluminum or an organolithium.

With respect to supported heterogeneous catalysts (1), non-supported catalysts (2) have the benefit of a greater activity. This is a significant advantage as it allows blander hydrogenation conditions to be used, with smaller quantities of catalyst.

EP-A-434.469 describes a catalytic composition which comprises (a) at least one titanium bis-cyclopentadienyl derivative and (b) at least one compound selected from those having general formula (i) $M^1(AlR^1R^2R^3R^4)$ and (ii) $M^1(MgR^5R^6R^7)$, wherein $M^1$, is selected from lithium, sodium and potassium. Compound (i) can be obtained by the reaction of an organic compound of an alkaline metal with an organometallic derivative of aluminum, whereas compound (ii) can be obtained by the reaction of an organo-alkaline compound with an organo-magnesium derivative.

EP-A-601.953 describes a hydrogenation process carried out in the presence of a catalyst having the general formula $Cp_2Ti(Pho)_2$ or $Cp_2Ti(CH_2PPh_2)_2$, wherein Cp is $C_5H_5$.

The above catalysts based on titanium are characterized by the presence of groups of the cyclopentadienyl type coordinated to the metal atom. In accordance with this it is generally thought that the active catalytic species consists of a stabilized titanium complex having a reduced oxidation state. These catalysts however have catalytic activities and a durability (average life of the catalyst during the hydrogenation) which are still unsatisfactory for normal industrial processes, in many cases requiring the use of high quantities of metal with the consequent serious contamination of the hydrogenated product. This particularly occurs when the solvent in which the hydrogenation process is carried out is an aliphatic hydrocarbon, such as cyclohexane or heptane, which, on the other hand, is preferable as a solvent compared to aromatic hydrocarbons owing to its greater volatility and lower toxicity.

In addition, it has also been observed that, when the above complexes of the metallocene type are used as hydrogenation catalysts, a significant isomerization reaction of the unsaturated hydrocarbons parallelly takes place, obtaining at times high percentages of product different from that desired. This has the double disadvantage of a decrease in the selectivity and greater difficulty in separating the undesired products.

Compositions are also known which are based on non-metallocene compounds of transition metals and alkyl derivatives of aluminum as activators, which have a certain catalytic activity in hydrogenation reactions. The publication Journal of the American Chemical Society, Vol. 85 (1963), page 4014 onwards., describes in particular catalytic compositions for the hydrogenation of unsaturated aliphatic substrates, based on titanium alkoxides and aluminum alkyls or lithium alkyls. The catalytic activity of these compositions however is insufficient for convenient use on an industrial scale. The same publication also mentions that the substitution of the aluminum alkyl activator with equivalent quantities of a Grignard reagent (butylmagnesium bromide) leads to the total deactivation of the catalyst.

The Applicant has now surprisingly found that it is possible to obtain a composition based on titanium or zirconium, which is capable of catalyzing the selective hydrogenation of olefinic double bonds and overcomes the above disadvantages, obtaining significantly higher catalytic activities than those so far registered in the known art for analogous systems. In addition, this composition does not contain metals with a high toxicity such as Cr, Pt, Ni, and can be used with fewer problems also in the food industry.

In accordance with this, the present invention relates to a catalytic composition effective in the selective hydrogenation of olefinic double bonds, comprising the reaction product between:

(A) at least one complex of a transition metal having the following general formula (I):

$$M(R^1)(R^2)(R^3)(R^4) \qquad (I)$$

wherein: M is selected from titanium and zirconium, preferably titanium;
each of the radicals $R^1$, $R^2$, $R^3$ or $R^4$, independently, represents an organic or inorganic group of an anionic nature σ-bonded to M, and may, particularly, be hydride, halide, a $C_1$–$C_{10}$ alkyl group, a $C_2$–$C_{15}$ alkylsilyl group, a $C_5$–$C_{15}$ cycloalkyl group, a $C_6$–$C_{15}$ aryl group, a $C_1$–$C_{15}$ alkoxyl group, a $C_1$–$C_{15}$ carboxyl group, a $C_2$–$C_{15}$ dialkylamide group and a $C_4$–$C_{20}$ alkylsilylamide group; on the condition that at least one, and preferably at least two, of these radicals is an organic group; and (B) at least one organometallic compound of magnesium having the following formula (II):

$$Mg(R^5)_n(R^6)_{(2-n)} \qquad (II)$$

wherein: $R^5$ or $R^6$ each independently represent an aliphatic or aromatic hydrocarbon group having from 1 to 20 carbon atoms, and
"n" is a decimal number between 0 and 2.0.

A second aspect of the present invention relates to a process for the preparation of said catalyst, comprising, in particular, putting the above compounds having formulae (I) and (II) in contact and reacting with each other, preferably in the presence of a liquid medium as diluent.

A further aspect of the present invention relates to a selective hydrogenation process of the olefinic double bonds of an olefinically unsaturated substrate, comprising putting said substrate in contact and reacting with hydrogen under appropriate conditions of pressure and temperature, in the presence of said catalyst and, optionally, an inert diluent which is normally a solvent of the substrate to be hydrogenated.

The compounds having formula (I) which form component (A) of the catalytic composition of the present invention belong to known groups of derivatives of titanium and zirconium and are normally in the solid or liquid state at room temperature. The methods for the preparation of many of these are described in specific literature together with the physico-chemical properties. However the compounds not described in literature can also be prepared analogously to the known methods.

According to the present invention, each R radical ($R=R^1$, $R^2$, $R^3$ or $R^4$) in formula (I) may independently be of an organic or inorganic nature but must be bonded to the metal M with a covalent (or also covalent-ionic) bond of the "σ" type, having a cylindrical symmetry.

Bonds of the "π" type are therefore excluded, such as, for example, the bond of a cyclopentadienyl group in a metallocene derivative. In addition, in the compound having formula (I), at least one R group of an organic nature must be present, i.e. containing at least one carbon atombonded to a hydrogen atom. In a preferred embodiment, at least two R groups are of an organic nature and, more preferably, all four R groups are of an organic nature.

Inorganic R groups are, for example, hydride, halides, particularly chloride and bromide, nitrates and nitrites, —$N_3$ azide, —$N_2H_2$ hydrazide, —$NH_2$ amide, —$CO_3H$ hydrogencarbonate, oxalate groups, etc.

R groups having formula (I) of an organic nature are, for example, alkyls, aryls, alkylsilyls, carboxylates, amides, alcoholates, thiols and β-diketonates. Also included in the scope of the present invention are compounds having formula (I) in which two R groups (or also three of these groups, when this is compatible with the steric characteristics of the compound) can be joined to each other to form a cyclic structure comprising the metal M itself.

Preferred organic R groups are those selected from $C_1$–$C_{10}$ alkyl, $C_2$–$C_{15}$ alkylsilyl, $C_5$–$C_{15}$ cycloalkyl, $C_6$–$C_{15}$ aryl, $C_1$–$C_{15}$ alkoxyl, $C_1$–$C_{15}$ carboxyl, $C_2$–$C_{15}$ dialkylamide and $C_4$–$C_{20}$ alkylsilylamide groups. Particularly preferred groups are aliphatic or cycloaliphatic, linear or branched, alcoholate or carboxylate groups such as, for example, methoxide, ethoxide, propoxide, isopropoxide, butoxide, trifluoromethoxide, cyclohexyloxide, octyloxide, diethyleneglycoldioxide and similar alkoxides, acetate, trifluoroacetate, butyrate, octanoate, versatate, cyclohexanoate and similar carboxylates. Even more preferred, for the purposes of the present invention are compounds having formula (I) in which at least two R groups, even better all R groups, are alcoholates.

Typical non-limiting examples of compounds having formula (I) which can be used for the formation of the catalytic composition of the present invention are listed hereunder:

Ti(OCH$_3$)$_4$  Ti(OC$_2$H$_5$)$_4$

Ti(OC$_4$H$_9$)$_4$  TiO(acetylacetonate)$_2$

Ti(OCOC$_3$)$_4$  Ti[OCON($^i$pr)$_2$]$_4$

Ti[N(CH$_3$)$_2$]$_4$  Ti(C$_6$H$_5$)$_4$

Ti(OC$_6$H$_5$)$_4$  TiCl$_2$(β-dinaphtholate)

According to the present invention, the above compounds having formula (I) can be used in pure form, or supported on an inert solid medium consisting, for example, of a porous inorganic solid, such as silica, alumina, silicoaluminates, optionally dehydrated and activated according to the methods known in the art, or consisting of a polymeric organic solid such as polystyrene, so as to obtain, at the end of the preparation, a supported catalytic composition. In this case the compounds having formula (I) are present in an adsorbed form on the surface of the organic or inorganic solid, but they can also be more stably bound to the solid by means of a covalent bond, as described in specific literature.

The organo-magnesium derivatives having formula (II) are typically selected from magnesium dialkyls. This group of compounds is well-known to experts in the field and there are numerous methods for their preparation. Many of these magnesium compounds are commercial products, normally in the form of a solution in an inert aliphatic hydrocarbon. Among organometallic compounds of magnesium suitable for the preparation of the catalytic composition of the present invention, magnesium dialkyls are preferred, wherein $R^5$ and $R^6$ are independently selected from linear or branched $C_1$–$C_{16}$, preferably $C_1$–$C_{10}$ alkyls. Typical examples of magnesium dialkyls are magnesium di-n-butyl, magnesium di-isobutyl, magnesium di-isopropyl, magnesium butyl-isobutyl, magnesium di-cyclohexyl, magnesium butyl-octyl, magnesium diaryl and relative mixtures.

With respect to the magnesium compound having formula (II), which forms component (B) of the present catalytic composition, this is added to the reaction environment preferably in the form of a solution in an aliphatic or cycloaliphatic hydrocarbon solvent, such as for example, cyclohexane.

The catalytic composition of the present invention is obtained by means of a process in which the above components (A) and (B) are put in contact with each other, under such conditions as to produce a reaction. The molar ratio between the magnesium compound having formula (II) and the compound of titanium or zirconium having formula (I) is preferably between 1:1 and 20:1, more preferably between 2:1 and 10:1. The reaction product obtained, which forms the catalytic principle or one of its precursors, has not yet been sufficiently characterized, and only indirectly, by its use in hydrogenation catalysis.

Compound (I) in the formation of the catalytic composition of the present invention can be introduced in pure form, or, preferably, it can be dispersed in an inert liquid medium, either as a suspension, if insoluble in said liquid, or as a homogeneous solution when the liquid is a solvent of the compound having formula (I).

The diluent can also be introduced into the reaction container before charging both components (A) and (B). It must be inert towards the compounds having formulae (I) and (II). The diluent is preferably selected from aliphatic or cycloaliphatic saturated hydrocarbons having from 3 to 15 carbon atoms and relative mixtures. Typical examples of these diluents are propane, butane, n-hexane, n-pentane, iso-pentane, n-heptane, octanes, decanes, cyclopentane, variously alkylated cyclopentanes, cyclohexane, variously alkylated cyclohexanes, "isopar" (mixture of paraffins). The preferred diluent is cyclohexane.

Depending on the nature of groups $R^1$, $R^2$, $R^3$ and $R^4$, the solubility of the compound having formula (I) in the reaction diluent with the compound having formula (II) may vary considerably. Organic groups such as alcoholates or carboxylates increase the solubility of these complexes in aliphatic hydrocarbons. It has been observed however that in certain cases, at the end of the reaction of components (A) and (B), or, in any case, after contact of the catalyst with hydrogen, the active principle which is formed is of a solid nature, in the form of a fine particulate in suspension in the inert diluent which also forms the liquid medium in which the hydrogenation process preferably takes place.

The preparation of the catalytic composition of the present invention can optionally be carried out in the presence of an additive (C) consisting of a polar aprotic organic compound, preferably having from 2 to 30 carbon atoms, which has a stabilizing function of the catalytic site, whereas effects on its activity are not usually observed. Compounds of this type are also known as Lewis bases, and comprise different groups of aliphatic or aromatic organic compounds containing at least one heteroatom selected from N, P, O, S, As and Se.

Preferred additives (C) are ethers, such as for example, dimethylether, diethylether, di-n-propylether, diisopropylether, di-n-butylether, di-sec-butylether, di-t-butylether, diphenylether, methylethylether, ethylbutylether, butylvinylether, anisol, ethylphenyl ether, ethyleneglycoldimethylether, ethyleneglycoldiethylether, ethyleneglycol dibutylether, diethyleneglycoldimethylether, diethyleneglycoldiethylether, diethyleneglycoldibutylether, polyethyleneglycoldimethylethers, polyethyleneglycoldiethylether, polyethyleneglycoldibutylether, tetrahydrofuran, alpha-methoxytetrahydrofuran, ethers of 2-hydroxymethyltetrahydrofuran, pyrane, dioxane, di(tetrahydrofuran)propane. Particularly preferred are cyclic ethers, such as tetrahydrofuran or pyrane and di- or poly-ethers, such as $C_1$–$C_{20}$ ethers of ethylene glycol and diethyleneglycol, even more preferred are $C_1$–$C_4$ ethers of glycol and ethylene diglycol.

The molar ratio M/(C) between the metal M and the additive (C), when the latter is present, is preferably higher than 0.01. This ratio is more preferably between 0.1 and 100; for ratio values higher than 100, the possible advantageous effect of the co-ordinating compound is no longer significant. Particularly preferred ratios are between 1 and 20.0.

The modifier (C) can be added as such or, preferably, in an aliphatic or cycloaliphatic hydrocarbon solution, more preferably mixed with component (A). Alternatively, the modifier (C) can be introduced into the reaction environment together with the compound having formula (II), or separately, diluted in the solvent used for the hydrogenation process.

According to a particular aspect of the present invention, the above components (A), (B) and, optionally, (C), are put in contact and reacted with each other in the presence of an aromatic hydrocarbon, normally mixed with the reaction diluent. This aromatic hydrocarbon is preferably present in such quantities as to have a molar ratio with respect to the metal M of component (A) ranging from 10 to 1000, and is selected from compounds having from 6 to 20 carbon atoms, such as, for example, toluene, xylenes, ethylbenzene, 6-dodecylbenzene, naphthalene, tetraline, biphenyl, indane and their mixtures.

Under the above conditions, at the end of the contact between the reagents, a finely subdivided, dark-coloured, from brown to purplish-brown, suspension is preferably formed. Depending on the nature of the components and reactions conditions, a homogeneous solution may initally be formed which subsequently becomes a suspension.

As far as the temperature and reaction times between (A) and (B) are concerned, these are not particularly critical and are within wide limits, to obtain the catalyst of the present invention. It is preferable however for the temperature to be between 0° C. and 100° C., more preferably between 20° C. and 70° C. The contact time between the reagents, which in practice is the activation time of the catalytic system, is appropriately selected in relation to the temperature and other reaction conditions (especially in relation to the possible presence of hydrogen and the additive (C)), and ranges from a few minutes to several hours, usually over 10 minutes and up to 20 hours, preferably from 1 to 10 hours.

The preparation of the catalyst must be carried out in an inert atmosphere. The term "inert atmosphere" refers to an atmosphere of gases which do not react with any of the species present in the reaction environment. Typical examples of these gases are helium, neon, argon, and relative mixtures. Alternatively hydrogen can also be used. Air and oxygen are not appropriate because they oxidate or decompose the hydrogenation catalyst making it inactive. Nitrogen is also not appropriate as in certain cases it may react with the activated form of the catalyst, causing undesired modifications.

According to another embodiment of the present invention, the catalytic composition in question can be prepared in the presence of the unsaturated compound which is to be hydrogenated. The latter can form the diluent itself in which the preparation of the catalyst is effected, or it can be mixed with an inert diluent of the type described above. In particular, the compound to be hydrogenated can be added entirely or partially to component (A) before the reaction with component (B). Alternatively, the unsaturated compound is added after contact between (A) and (B), but before introducing the hydrogen. In another variation of the present invention, (A) and (B) are put in contact with each other in an atmosphere of hydrogen and the substrate is subsequently introduced.

The present invention also relates to a process for the selective hydrogenation of olefinic double bonds in unsaturated organic substrates, which comprises putting the substrate to be hydrogenated in contact with hydrogen, preferably in a suitable liquid medium, in the presence of the catalytic composition described above, for a period sufficient to obtain the desired hydrogenation degree. This is normally as high as possible and generally exceeds 90%, preferably 97%, referring to the disappearance of olefinic double bonds. The scope of the present invention does not exclude however partial hydrogenation processes of the substrate, in the presence of the catalytic composition in question.

Among the various substrates which can be hydrogenated in accordance with the process of the present invention, those whose molecule comprises from 2 to 100 carbon atoms, preferably from 4 to 50 carbon atoms are preferred. More preferably, these substrates to be hydrogenated have at least one primary olefinically unsaturated bond, i.e. comprising the radical $=CH_2$ or the radical $\equiv CH$. Typical substrates which can be hydrogenated with the process of the present invention are the usual aliphatic or aromatic olefins having from 2 to 50, preferably from 4 to 25, carbon atoms, such as, for example, 1-butene, isobutene, 1-octene, cyclohexene, cyclohexadiene, undecene, cyclododecatetraene, norbornene, styrene (selective hydrogenation to ethylbenzene), divinylbenzenes, indene, conjugated dienes such as butadiene, isoprene, chloroprene, non-conjugated dienes such as ethylidenenorbornadiene, 1,4-hexadiene and the like, acetylene derivatives such as acetylene, 2-butine, 1-hexine. Equally suitable as substrates are also olefins and styrene derivatives comprising heteroatoms such as, for example, halogens, especially chlorine and fluorine, silicon, boron, sulfur, oxygen. Other unsaturatetd substrates consist, for example, of esters of unsaturated fatty acids, such as linoleic or ricinoleic acids, esters of unsaturated acids with a short chain such as, for example, acrylic, methacrylic, maleic or fumaric acid, vinyl esters of aliphatic or aromatic acids, organic imines (also commonly called Schiff bases).

The hydrogenation of these substrates can be carried out in an inert diluent medium, or also on the compound to be hydrogenated as such. The process can be carried out in suitable reactors, under hydrogen pressure usually ranging from 0.1 to 10 MPa, at temperatures ranging from 0 to 150° C., preferably between 50 and 120° C., and for times less than 5 hours, more preferably between 30 minutes and 120 minutes, depending on the substrate to be hydrogenated and the hydrogenation degree desired. Blander conditions can be used, for example, if a primary double bond is to be hydrogenated, leaving a secondary one intact in a nonconjugated diene.

According to an embodiment, the solution of the substrate to be hydrogenated is charged, under a hydrogen atmosphere, into the hydrogenation reactor followed by the catalytic composition dispersed in the diluent. The whole mixture is then pressurized with hydrogen and brought to the desired temperature. When the hydrogenation is complete, the hydrogenated product is recovered according to the known techniques which comprise, for example, distillation of the solvent, or distillation of the hydrogenated substrate.

The catalytic compositions which can be obtained with the process of the present invention are also active in the hydrogenation process in very low quantities, indicatively up to 10 ppm of M with respect to the substrate to be subjected to hydrogenation, with a ratio between moles of metal M and olefinic double bonds of up to 1:60,000. This is a definite advantage with respect to the catalysts of the known art. It should also be pointed out that the hydrogenation process of the present invention allows the hydrogenated product to be obtained without producing significant quantities of isomerization product.

The present invention is further illustrated by the following examples which however in no way restrict the overall scope of the invention itself.

COMPARATIVE EXAMPLES 1–3 AND EXAMPLES 4–16

The general procedure adopted for carrying out the experiments described in examples 1 to 16 is specified hereunder. Table 1 below summarizes the data and the quantitative and qualitative results relating to each example, together with any variations in the general procedure.

PREPARATION OF THE CATALYTIC COMPOSITION 0.12 mmoles of the compound having formula (I) which forms component (A), 20 ml of anhydrous cyclohexane, optionally the activator (C) as an 0.45 M solution in anhydrous cyclohexane, and 0.72 ml of a 1 M solution of $Mg(butyl)_2$ in n-heptane, which forms component (B), are charged, in an argon atmosphere, into a tailed test-tube equipped with a magnetic stirrer. The mixture is left under stirring for 2 hours at room temperature.

HYDROGENATION REACTION

The catalytic solution prepared as above is siphoned in a 100 ml autoclave previously maintained under argon. The unsaturated substrate to be hydrogenated, previously distilled and conserved on molecular sieves, is then charged. The autoclave is pressurized with 50 atm of hydrogen and brought to a temperature of 60° C. by heating with a bath. The hydrogenation is carried out under these conditions for a duration of 90 minutes, continuously feeding hydrogen to keep the pressure value constant.

At the end of the reaction, the autoclave is unloaded, operating in an atmosphere of air, obtaining a spongy, dark-coloured suspension which becomes pale yellow on contact with air. The suspended particulate (catalyst residue) is separated by sedimentation and the solution obtained is analyzed by gaschromatography and gas-mass to determine the content of hydrogenated substrate and possible isomers. The results are summarized in table 1 below.

TABLE 1

Hydrogenation of unsaturated substrates in cyclohexane

| Example | Olefin | Component (A) | Additive (C) | Activation time (h) | (moles Mg)/ (moles Ti) | Isomers (%) | Yield (%) | Notes |
|---|---|---|---|---|---|---|---|---|
| 1(*) | 1-octene | $TiCl_4$ | DME | 20 | 6 | 4 | 37.5 | — |
| 2(*) | 1-octene | $TiCl_4$ | DBG | 20 | 6 | 6 | 48 | — |
| 3(*) | 1-octene | $TiCl_4$ | DBG | 2 | 6 | 1.5 | 15 | activation at 70° C. |
| 4 | 1-octene | $Ti(O-Bu)_4$ | DBG | 20 | 6 | 9.9 | 90 | — |
| 5 | 1-octene | $Ti(O-Bu)_4$ | DBG | 20 | 6 | n.d. | 100 | activation in the presence of 1-octene |
| 6 | 1-octene | $Ti(O-Bu)_4$ | — | 2 | 6 | n.d. | 100 | — |
| 7 | 1-octene | $Ti(O-Isopr)_4$ | DBG | 2 | 6 | n.d. | 100 | — |
| 8 | 1-octene | $Ti(O-Bu)_4$ | DBG | 2 | 6 | n.d. | 100 | activation at reflux |
| 9 | 1-octene | $Ti(O-Bu)_4$ | DBG | 2 | 6 | n.d. | 100 | cyclohexane = 100 ml |
| 10 | 1-octene | $Ti(O-Bu)_4$ | DBG | 2 | 6 | <1 | 99 | 1-octene/Ti = 10,000 |
| 11 | 1-octene | $Ti(O-Bu)_4$ | — | 2 | 1 | 11 | 58 | — |
| 12 | 1-octene | $Ti(O-Bu)_4$ | — | 2 | 2 | 7.5 | 92 | — |
| 13 | 1-octene | $Ti(O-Bu)_4$ | — | 2 | 3 | n.d. | 100 | — |
| 14 | 1-octene | $Ti(O-Bu)_4$ | — | 2 | 3 | 2.7 | 97.2 | 1-octene/Ti = 10,000 |
| 15 | cyclooctene | $Ti(O-Bu)_4$ | — | 2 | 3 | <1 | 76 | — |
| 16 | isoprene | $Ti(O-Bu)_4$ | — | 2 | 6 | n.d. | 23.4 | — |

Conditions: Cyclohexane = 20 ml; olefin = 120 mmoli; molar ratio olefin/Ti = 1000; component (B) = Dibutylmagnesium; pressure = 5 MPa; temp. = 60° C.; duration = 90 minutes; atomic ratio Mg/Ti = 6; molar ratio Ti/(C) = 9
Abbreviations: (*) = Comparative Example; DME = Dimethylether; DBG = Diethylenglycoldibutylether; n.d. = not determined

What is claimed is:

1. A process for the selective hydrogenation of an olefinic double bond of an olefinically unsaturated substrate, comprising:

contacting said substrate with hydrogen;

reacting said substrate with said hydrogen in the presence of a catalytic composition comprising the reaction product between:

(A) at least one complex of a transition metal having formula (I):

$$M(R^1)(R^2)(R^3)(R^4) \qquad (I)$$

wherein
M is a metal selected from the group consisting of titanium and zirconium;
each of the radicals $R^1$, $R^2$, $R^3$ or $R^4$ independently represents an anionic organic group σ-bonded to M or an anionic inorganic group σ-bonded to M;
wherein at least one of said radicals $R^1$, $R^2$, $R^3$ and $R^4$ is an organic group; and (B) at least one organometallic magnesium compound of formula (II):

$$Mg(R^5)_n(R^6)_{(2-n)} \qquad (II)$$

wherein $R^5$ or $R^6$ each independently represent an aliphatic or aromatic hydrocarbon group having from 1 to 20 carbon atoms; and
wherein n is a decimal number between 0 and 2.0.

2. The process according to claim 1, wherein said substrate comprises from 2 to 100 carbon atoms and consists of an aliphatic olefin having from 2 to 100 carbon atoms, an aromatic olefin having from 2 to 100 carbon atoms, an ester of an unsaturated carboxylic acid with an aromatic alcohol, an ester of an unsaturated carboxylic acid with an aliphatic alcohol, an ester of an unsaturated carboxylic acid with a phenol, a vinyl ester of an aliphatic acid, a vinyl ester of an aliphatic acid, a vinyl ester of an aromatic acid or an organic imine.

3. The process according to claim 1, wherein said reacting with said hydrogen is carried out under a hydrogen pressure of from 0.1 to 10 MPa;
wherein a temperature is of 0 to 150° C.; and
wherein a molar ratio between metal M and said olefinic double bond of said olefinically unsaturated substrate is up to 1:60,000.

4. The process according to claim 1, wherein at least two of said radicals $R^1$, $R^2$, $R^3$ and $R^4$ are an organic group.

5. The process according to claim 1, wherein $R^6$ and $R^5$ in said formula (II) are independently linear or branched aliphatic hydrocarbon groups having from 2 to 10 carbon atoms.

6. The process according to claim 1, wherein n in said formula (II) is equal to 2.

7. The process according to claim 1, wherein said complex of formula (I) is dispersed in an inert liquid medium selected from the group consisting of an aliphatic saturated hydrocarbon, a cycloaliphatic saturated hydrocarbon and mixtures thereof.

8. The process according to claim 1, wherein said radicals $R^1$, $R^2$, $R^3$ and $R^4$ in said formula (I) are the same; and
wherein said radicals $R^1$, $R^2$, $R^3$ and $R^4$ are selected from the group consisting of a carboxylate, an amide, an alcoholate and a β-diketonate.

9. The process according to claim 1, wherein a molar ratio between the magnesium compound of formula (II) and the compound of formula (I) is between 1:1 and 20:1.

10. The process according to claim 1, wherein said metal M in said formula (I) is titanium and a molar ratio between magnesium and titanium is between 2:1 and 10:1.

11. The process according to claim to claim 1, wherein said catalytic composition further comprises an additive (C).

12. The process according to claim 11, wherein said additive is a polar aprotic organic compound having from 2 to 30 carbon atoms.

13. The process according to claim 11, wherein said additive is an aliphatic or aromatic ether; and
wherein a molar ratio between said metal M in said formula (I) and said additive is between 0.1 and 100.

14. The process according to claim to claim 1, wherein in formula (I) each $R^1$, $R^2$, $R^3$ or $R^4$, is independently selected from the group consisting of a hydride, a halide, a $C_1$–$C_8$ alkyl group, a $C_3$–$C_{15}$ alkylsilyl group, a $C_5$–$C_8$ cycloalkyl group, a $C_6$–$C_{10}$ aryl group, a $C_1$–$C_8$ alkoxyl group, a $C_1$–$C_8$ carboxyl group, a $C_2$–$C_{10}$ dialkylamide group and a $C_4$–$C_{20}$ alkylsilylamide group.

* * * * *